(12) United States Patent
Bates (10) Patent No.: US 7,651,696 B2
(45) Date of Patent: *Jan. 26, 2010

(54) IMPLANTABLE DEVICE FOR TREATING DISEASE STATES AND METHODS OF USING SAME

(75) Inventor: Mark C. Bates, Charleston, VA (US)

(73) Assignee: Nexeon Medical Systems, Inc., Charleston, WV (US)

( * ) Notice: Subject to any disclaimer, the term of this patent is extended or adjusted under 35 U.S.C. 154(b) by 937 days.

This patent is subject to a terminal disclaimer.

(21) Appl. No.: 10/864,936

(22) Filed: Jun. 9, 2004

(65) Prior Publication Data

US 2005/0064009 A1    Mar. 24, 2005

Related U.S. Application Data

(63) Continuation of application No. 09/648,257, filed on Aug. 25, 2000, now Pat. No. 6,740,331.

(51) Int. Cl.
*A61F 2/04* (2006.01)
*A61F 2/06* (2006.01)

(52) U.S. Cl. .................... 424/423; 424/426
(58) Field of Classification Search .............. None
See application file for complete search history.

(56) References Cited

U.S. PATENT DOCUMENTS

| 4,619,246 A | 10/1986 | Molgaard-Nielsen et al. |
| 5,180,368 A | 1/1993 | Garrison |
| 5,328,470 A | 7/1994 | Nabel et al. |
| 5,603,694 A | 2/1997 | Brown et al. |
| 5,713,863 A | 2/1998 | Vigil et al. |
| 5,800,507 A | 9/1998 | Schwartz |

(Continued)

FOREIGN PATENT DOCUMENTS

FR    2 764 503 A1    12/1998

(Continued)

OTHER PUBLICATIONS

USPTO Non-Final Office Action for U.S. Appl. No. 09/648,257, 8 pages (mailed Nov. 6, 2002).

(Continued)

*Primary Examiner*—Carlos A. Azpuru
(74) *Attorney, Agent, or Firm*—Jones Day; Nicola A. Pisano; Jaime D. Choi (57) ABSTRACT

Methods and apparatus are provided for delivering drugs, gene vectors, naturally-occurring or synthetic hormones or proteins or other bioactive agents within a patient's vasculature. In a preferred embodiment, the apparatus comprises a material that elutes or secretes a bioactive agent and is held in place within the patient's vessel by an anchor. The material may comprise a biocompatible, and optionally, absorbable matrix, or a culture medium that sustains and nourishes stem cells, spleen cells or pancreatic islets or other beneficial cells. The anchor and material are sized and/or collapsible from a delivery configuration, in which the anchor and material may be delivered into the patient's vasculature within a delivery sheath, to a deployed configuration, wherein the anchor engages an interior wall of the patient's vessel. The apparatus of the invention may be temporarily or permanently implanted, and may in addition self reconfigure after a predetermined period of residency.

20 Claims, 10 Drawing Sheets

U.S. PATENT DOCUMENTS

| | | | |
|---|---|---|---|
| 5,911,704 | A | 6/1999 | Humes |
| 6,245,012 | B1 | 6/2001 | Kleshinski |
| 6,280,414 | B1 | 8/2001 | Shah et al. |
| 6,740,331 | B1 * | 5/2004 | Bates et al. ............ 424/423 |
| 2001/0001817 | A1 | 5/2001 | Humes |
| 2002/0090388 | A1 | 7/2002 | Humes et al. |
| 2004/0193137 | A1 | 9/2004 | Bates |

FOREIGN PATENT DOCUMENTS

| | | | |
|---|---|---|---|
| WO | WO 96/39098 A | 12/1996 | |

OTHER PUBLICATIONS

USPTO Notice of Allowance for U.S. Appl. No. 09/648,257, 8 pages (mailed Jan. 9, 2004).

USPTO Non-Final Office Action for U.S. Appl. No. 10/822,037, 5 pages (mailed May 2, 2007).

USPTO Final Office Action for U.S. Appl. No. 10/822,037, 7 pages (mailed Apr. 29, 2008).

USPTO Non-Final Office Action for U.S. Appl. No. 10/822,037, 6 pages (mailed Sep. 3, 2008).

USPTO Final Office Action for U.S. Appl. No. 10/822,037, 8 pages (mailed Mar. 9, 2009).

* cited by examiner

IMPLANTABLE DEVICE FOR TREATING DISEASE STATES AND METHODS OF USING SAME

This application is a continuation of U.S. application Ser. No. 09/648,257 filed Aug. 25, 2000, now allowed as U.S. Pat. No. 6,740,331.

FIELD OF THE INVENTION

This invention relates to apparatus for treating various disease states by providing drug delivery, gene therapy or aggregations of bioactive substances, including cells and components thereof. More particularly, the present invention provides methods and implantable devices for therapeutic intervention including but not limited to delivery of drugs, gene therapy, or other bioactive substances, into a patient's vasculature for local or systemic therapy. The implantable device also provides a platform for centering diagnostic sensors in a vessel for the purpose of transmitting hemodynamic or other physiologic data to a receiver outside the body.

BACKGROUND OF THE INVENTION

According to the National Cancer Institute, approximately 4,000 specific conditions are known to be caused by genetic detects. The GeneMed Network states that each human being carries roughly a half dozen defective genes, and that about one in ten people has or will develop an inherited genetic disorder.

A composite of approximately 150,000 individual genes constitutes a human being. Variation in the structure of these genes can lead to disease. Many diseases are hereditively passed by a single gene, while many others are influenced by a collection of genes.

Several years ago, the Human Genome Project began mapping every human gene. The project is fostering an understanding of the very foundation of human disease and is enabling new therapies to treat and predict the onset of disease. One such therapy is gene therapy, which seeks to directly and beneficially modify the expression of genes through delivery of engineered genetic material. Foreign nucleotide sequences of either DNA or RNA are inserted into a patient's cells to result in either expression of non-integrated sequences or integration of sequences directly into the DNA of the cells.

Safe and efficient delivery of nucleotide sequences to appropriate cells poses one of the primary challenges to gene therapy. Vectors, which encapsulate therapeutic genes, have been developed to deliver the sequences. These vectors may be either viral or synthetic. Viral vectors, derived from viruses, are the primary vectors in experimental use today. Viruses efficiently target cells and deliver genome, which normally leads to disease. However, viral vectors for gene therapy are modified so that they may not cause disease. Rather, therapeutic recombinant genes are inserted into the vectors and delivered to target cells. Optimally, the modified viruses retain their ability to efficiently deliver genetic material while being unable to replicate.

Research in the field of gene therapy is still in the formative stages. Human trials only began in 1990 with ex vivo techniques, wherein a patient's cells were harvested and cultivated in a laboratory and incubated with vectors to modify their genes. Cells were then harvested and intramuscularly transplanted back into the patient. Trials quickly shifted to in vivo techniques, in which viral vectors are administered directly to patients, again intramuscularly. A variety of diseases are currently being evaluated as candidates for gene therapy, and a need exists in the art for improved vector delivery techniques.

While significant progress has been made, current gene therapy delivery techniques have many drawbacks. Viral vectors are inherently dangerous due to the innate ability of viruses to transmit disease. Furthermore, long-term effects of using viruses as delivery vehicles are unclear. Chances for error in modifying the viruses to vectors are significant, and consequences may be substantial, including potential irreversible alteration of the human gene pool. Also, delivery of the vectors to an efficacious portion of diseased cells has proven difficult and expensive.

Synthetic vectors have been developed to address the potential for disease transmission with viral vectors. These vectors are complexes of DNA, proteins, or lipids, formed in particles capable of efficiently transferring genes. However, synthetic vectors have thus far proved less effective than viral vectors and have been slower to gain acceptance.

Perhaps even more problematic than limitations of the vectors, intramuscular in vivo techniques, wherein vectors are delivered into a patient's muscle tissue, have proven somewhat ineffective in clinical use. Systemic expression of inserted sequences is not realistic since therapy is localized.

In view of the drawbacks associated with previously known methods for delivery of gene therapy, it would be desirable to provide methods and apparatus that overcome such drawbacks.

In addition to gene therapy techniques, research has focused on the selective implantation or injection of cells or specific proteins to mitigate disease states, cause tissue regeneration or improve organ function. For example, researchers have investigated improvement of cardiac function by injecting cells via epicardial, endocardial or coronary sinus access routes into the myocardium. See, e.g., Thompson, C. A., et al., *Percutaneous Transvenous Cellular Cardiomyoplasty, A Novel Nonsurgical Approach for Myocardial Cell Transplantation*, J. Am. Coll. Card., 41(11):1964-71 (2003).

Others have investigated injecting cells into the pancreas or liver to improve insulin production in diabetics. Kodama et al., *Islet Regeneration During the Reversal of Autoimmune Diabetes in NOD Mice*, Science, 302(5648):1223-1227 (2003), describes the injection of donor spleen cells from non-diabetic mice into diabetic mice so that a protein complex secreted by the spleen cells could mitigate the autoimmune disorder causing diabetes. Hering, B. J., et al., *Transplantation of cultured islets from two-layer preserved pancreases in type 1 diabetes with anti-CD3 antibody*, Am. J. Transplant. 4(3):390-401 (2003), describes infusion of isolated islets of Langerhans into a patient to alleviate Type-I diabetes. Panaro, F., et al., *Auto-islet transplantation after pancreatectomy*, Expert Opin. Biol. Ther., 3(2):207-14 (2003), describes the infusion of isolated islet cells through a catheter and into a vein in a patient's liver following partial pancreatectomy, so that the islets graft onto and function similarly to the removed liver.

Still others have discovered that certain proteins, such as apolipoprotein A-I Milano, when introduced into the rats fed a high cholesterol diet, inhibits the onset of arterial thrombus formation, as reported in Li, D. et al., *Inhibition of arterial thrombus formation by ApoAl Milano*, Arterioscler. Thromb. Vasc. Biol., 19:378-83 (1999). Chiesa, G. and Sirtori, C. R., report in *Apolipoprotein A-I(Milano): current perspectives*, Curr. Opin. Lipidol. 14:159-63 (2003) that recombinant apolipoprotein A-I (Milano), formulated as synthetic HDL with phospholipids, appears to exert a direct removing effect on arterial cholesterol when infused into subjects at different doses.

In view of the foregoing, it further would be desirable to provide methods and apparatus for delivering cells, cell components or naturally-occurring or synthetic proteins into the vascular system of a patient to achieve a treatment goal.

It still further would be desirable to provide methods and apparatus for providing localized delivery of genes, cells or bioactive agents into a patient's vascular system that have a preselected residency beyond that obtainable by systemic or localized intravascular infusions.

It also would be desirable to provide methods and apparatus for delivering viral vectors, synthetic vectors, drugs, cells, or naturally-occurring or synthetic proteins or other therapeutic agents in a manner that nourishes and sustain production and secretion of the therapeutic agents in vivo.

It would also be desirable to provide methods and apparatus for delivering bioactive agents intravascularly, wherein, once the efficacious agent has dispersed, the delivery system reconfigures to mitigate risk of complication to the patient.

SUMMARY OF THE INVENTION

In view of the foregoing, it is an object of the present invention to provide methods and apparatus for delivering cells, cell components or naturally-occurring or synthetic proteins into the vascular system of a patient to achieve a local or systemic treatment goal.

It is also an object of the present invention to provide methods and apparatus for providing localized delivery of genes, cells or bioactive agents into a patient's vascular system that have a preselected residency beyond that obtainable by systemic or localized intravascular infusions.

It is another object to provide relatively inexpensive methods and apparatus for delivering viral vectors, synthetic vectors, drugs, cells, or naturally-occurring or synthetic proteins or other therapeutic agents in a manner that nourishes and sustain production and secretion of the therapeutic agents in vivo.

It is yet another object to provide methods and apparatus for delivering bioactive agents intravascularly, wherein, once the efficacious agent has dispersed, the delivery system reconfigures to mitigate risk of complication to the patient.

These and other objects of the present invention are accomplished by providing methods and apparatus that expose one or more bioactive agents directly to a patient's bloodstream in a portion of the patient's vasculature that effects a diseased tissue organ. In a preferred embodiment, the apparatus comprises an implantable device that elutes or secretes a desired naturally-occurring or synthetic bioactive agent, such a drug, gene vector, protein or hormone. In accordance with the principles of the present invention, blood that comes into contact with the device is expected to absorb the bioactive agent and carry the agent to a tissue, organ, vessel or systemically.

In one embodiment intended for implantation over a period of time of weeks to months, the apparatus of the present invention comprises an eluting or secreting material held in place within a patient's vessel by an anchor. The anchor and eluting material are sized and/or expandable from a delivery configuration, suitable for transluminal delivery into the patient's vasculature within a delivery sheath, to a deployed configuration, wherein the device engages an interior wall of the patient's vessel.

Devices designed utilizing nanotechnology or MEMS may be used to sense pressure or other physiologic variables in a vessel. The present invention provides a way to center such a device inside a vessel. This may be desirable to prevent device migration and wedging into distal vessels while also allowing the easy deployment and retrieval of such a device. Without such a centering system the sensor will end in a distal vessel where thrombosis and inflammatory responses may encase the sensor and render useless or isolate it from the target circulatory circuit.

In accordance with the principles of the present invention, the eluting or secreting material may elute or secrete recombinant genes, drugs or other bioactive or therapeutic agents for a predetermined period of time, after which the material disperses. In this case, the anchor may reconfigure itself to minimize complications to the patient.

Alternatively, the eluting or secreting material disposed within the implantable device may comprise a culture material that nourishes and sustains the bioactive agent using nutrients provided by the patient's blood stream. For example, material disposed within the implantable device may comprise a culture that sustains islands of Langerhans or other endocrine cells, and thus secretes proteins or hormones required to cure or alleviate diabetes. As a further example, the implantable device may comprise a culture material that supports secretion of a beneficial protein, such as apolipoprotein A-I (Milano), which may be used to reverse the effects of atherosclerosis.

Methods of using the apparatus of present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 12A and 12B are side views of an apparatus for delivering a bioactive substance within a patient's bloodstream, wherein FIG. 12A depicts an expanded profile configuration and FIG. 12B depicts a reduced delivery profile;

DETAILED DESCRIPTION OF THE INVENTION

Figure 1A:
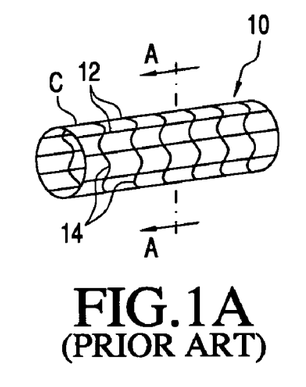
FIGS. 1A and 1B are views of a prior art eluting stent shown, respectively, in isometric view and in cross-section along view line A-A of FIG. 1A within a patient's vessel.
Figure 1B:
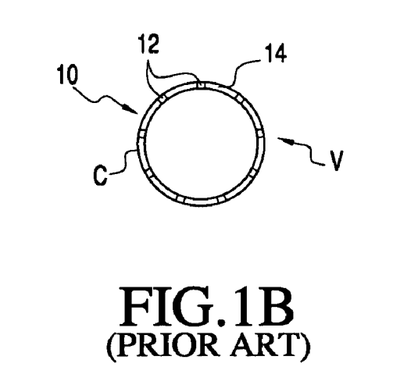

The present invention provides methods and apparatus for delivering naturally-occurring or synthetic bioactive agents, such a drug, gene vector, protein or hormone. Referring to FIG. 1, prior art apparatus for delivering a bioactive substance into a vessel is described. As shown in FIG. 1A, eluting stent 10 comprises linear members 12 and expandable radial members 14. Stent 10 is coated with coating C of a bioactive substance. Stent 10 is expanded within vessel V to engage an interior wall of the vessel, as seen in FIG. 1B. The bioactive substance of coating C is eluted into blood passing through vessel V.

Figure 2:
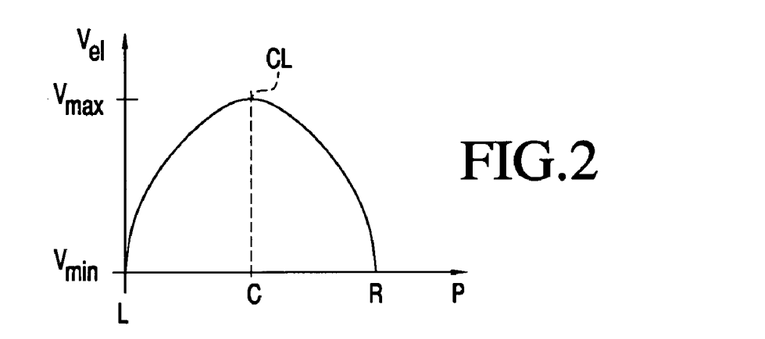
FIG. 2 is a graph illustrating velocity profile through a cross-section of a patient's vessel.

FIG. 2 graphs the velocity profile of bloodflow through a cross-section of vessel V. Bloodflow velocity Vel is presented as a function of position P within vessel V. Positions at the left wall L, center C, and right wall R of vessel V are labeled along the ordinate axis. Likewise, minimum velocity Vmin and maximum velocity Vmax are labeled along the abscissa axis. Note that minimum velocity Vmin occurs at the vessel wall. Velocity increases at positions distant from vessel V, reaching the maximum Vmax at the center C of the vessel. Blood thus establishes a cylindrical, 3-dimensional Poiseulle flow, as illustrated by revolving the graph of FIG. 2 about center line CL.

Stent 10 of FIG. 1B abuts against the interior wall of vessel V, where bloodflow velocity Vel approaches its minimum Vmin. The stent therefore is ineffective in delivering the bioactive substance of coating C to the bloodstream, since stent 10 is only exposed to a small, near-stagnant portion of blood flowing adjacent to the wall of vessel V.

Figure 3A:
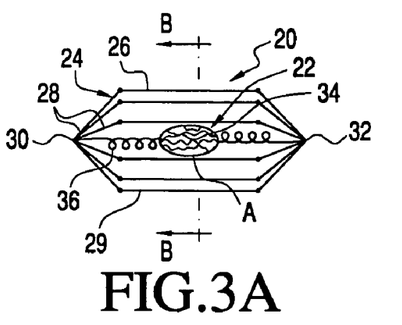
FIGS. 3A and 3B are views of apparatus constructed in accordance with the present invention shown, respectively, in side view in an expanded deployed configuration and in cross-section along view line B-B within a patient's vessel.
Figure 3B:
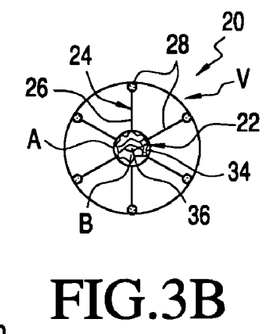

With reference now to FIGS. 3A and 3B, apparatus constructed in accordance with the principles of the present invention is described. Apparatus 20 is configured to deliver a bioactive substance to the bloodstream much more efficiently by exposing the substance to the bloodstream at areas distant from the vessel wall, where blood flows with higher velocity. Apparatus 20 comprises eluting or secreting material 22 disposed within anchor 24.

Anchor 24 comprises a collapsible cage that is adapted for semi-permanent or permanent implantation within a patient's vessel. The cage is formed from a plurality of preformed segments, wherein each segment has a longitudinally-extending portion 26 and a radially-extending portion 28. Radially-extending portions 28 are joined together at their proximal ends at joint 30 and at their distal ends at joint 32.

Anchor 24 preferably is fabricated from nickel-titanium wires, which may be welded at joints 30 and 32. The segments making up the anchor may be substantially straight, or together may have a sinusoidal shape, as discussed hereinbelow with respect to FIG. 4. Anchor 24 is able to resiliently self-expand from a delivery configuration, suited for transluminal insertion into a patient's vasculature, to the deployed configuration of FIG. 3A, wherein anchor 24 is adapted to engage an interior wall of the patient's vessel V, as seen in FIG. 3B. Optionally, anchor 24 may include barbs 29 that extend radially from longitudinally-extending portions 26 to prevent migration of the anchor once it is deployed in a vessel.

Material 22 comprises pellet 34, which is anchor 24 by filament 36 that holds the pellet away from the edges of the anchor. Illustratively, filament 36 comprises an extensible band of a biocompatible material such as stainless steel, a nickel titanium alloy, or a biocompatible polymer. Filament 36 also may apply a tensile force to anchor 24 to facilitate expansion of the anchor. Further, barbs or hooks may be added to the edges to further anchor the device and prevent migration in the midst of antigrade flow. Pellet 34 is sized such that it may initially be transluminally delivered into the patient's vasculature. Upon exposure to blood flow within vessel V, pellet 34 may expand such that it fills a substantial portion of the interior space of the anchor, and provides a high surface contact area for blood flowing at high velocity near the center of the vessel.

In accordance with the principles of the present invention, pellet 34 comprises a bioactive substance that elutes or secretes a bioactive agent, such as a gene therapy sequences (encapsulated within vectors or alone), drug, protein or hormone. For example, pellet 34 may comprise an aggregation of autologous or donor cells, such as spleen cells, stem cells, isolated pancreatic islets or other cells, disposed in a matrix of a biocompatible culture medium capable of propagating or secreting naturally-occurring or synthetic proteins or hormones. When delivered within the vasculature, blood contacts pellet 34, thereby exposing the cells, as well as downstream capillary beds, to the substance and providing localized or systemic therapy.

In the context of treatment of diabetes, pellet 34 may comprise a culture medium capable of nourishing and sustaining autologous or donor pancreatic cells or islets with nutrients extracted from the patient's bloodstream, and apparatus 20 may be implanted in an artery adjacent to the pancreas or hepatic vein. Also implantation in a vessel remote from the pancreas may provide an alternative to direct placement in the target endocrine organ. For example, the spleenic artery may be ideal allowing the protein aggregates and cell byproducts to be picked up by the spleen. In this manner, device 20 functions as a graft so that insulin secreted from the islets contained within pellet 34 is dispersed into the bloodstream. Alternatively, spleen cells may be used for a device implanted upstream of the pancreas, so that protein complexes secreted by the cells may mitigate the effects of an autoimmune disorder, as described in the above article by Kodama et al.

In the context of treating atherosclerosis, pellet 34 may comprise a culture medium capable of propagating and secreting apolipoprotein A-I (Milano) or other HDL-like analog. As for the pancreatic islets described in the preceding embodiment, the matrix comprising the pellet may be nourished with nutrients extracted from the patient's bloodstream. If implanted, for example, in a patient's vena cava or other venous structure, the apparatus of the present invention could propagate and disperse the desired proteins to the patient's bloodstream for a period of weeks to months, and thereby inhibit or even reverse the atherosclerotic process.

Alternatively, pellet 34 may comprise a bioabsorbable material loaded with a drug, gene vector, synthetic hormone or protein or other bioactive agent that releases the bioactive agent into the bloodstream as the material of the pellet dissolves. As a still further alternative, the bioactive agent may be eluted from the pellet, and the device later retrieved from the patient's vasculature. To assist in retrieval of anchor 24, the struts of anchor 24 may be coated or impregnated with a drug that prevents endothelialization, such as an anti-mitotic.

Optionally, apparatus 20 may further be impregnated or coated with an anti-clotting agent, such as heparin, coumadin, direct thrombin inhibitor, glycoprotein Iib/IIIa inhibitor or aspirin, to prevent clotting or thrombus build-up around radially-extending portions 28 or within pellet 34 or anchor 24. Alternatively, if apparatus 20 is intended to kill unwanted or diseased downstream tissue, anchor 24 and/or pellet 34 may be coated or impregnated with an agent that promotes targeted cell death or clotting-off of the vessel or target organ tributaries. The central location of pellet 34 within vessel V, as seen in FIG. 3B, contrasted with the location of coating C of stent 10 in FIG. 1B, illustrates a primary advantage of the present invention over previously known vascular elution techniques: the bioactive substance of apparatus 20 is exposed to bloodflow of relatively high velocity.

When used in drug delivery applications, the bioactive agent delivered from pellet 34 may, for example, comprise a therapeutic toxin, such as a chemotherapy drug. Drugs for chemotherapy are generally toxic to the entirety of an organism, not just cancer cells. Thus, delivery of these drugs directly into the vasculature, via sustained release in an arterial division supplying a tumor, is expected to provide more focused therapy. The bioactive agent alternatively may comprise antibiotics. In patients with, for example, a compromised immune system or deep seeded infection, delivery of antibiotics directly into an abscess or infected area may be beneficial.

Furthermore, prolonged systemic delivery of a desired bioactive agent may be accomplished through placement of apparatus 20 in a central vein of a patient's vasculature. Current techniques only provide sustained drug infusion through central intravenous ("IV") access, or through chronic, specifically-designed, IV devices. Conversely, apparatus 20 may be deployed in a central vein and then removed at a later time, for example, one to two weeks later. During that time period, apparatus 20 may provide systemic treatment to the patient, thereby eliminating the risk of infection from prolonged IV use.

Figure 4:
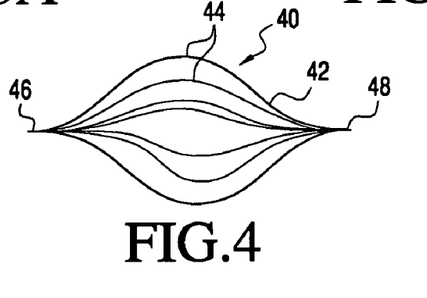
FIG. 4 is a side view of an alternative embodiment of the anchor of, the present invention in an expanded deployed configuration.

Referring to FIG. 4, an alternative anchor in accordance with the present invention is described. Anchor 40 comprises sinusoidal cage 42, which is adapted for use with an eluting or secreting material such as described hereinabove. Cage 42 is formed from a plurality of sinusoidal segments 44 that are joined at their proximal and distal ends at joints 46 and 48, respectively.

Segments 44 preferably are fabricated from nickel-titanium wires, which may be welded at joints 46 and 48. Like anchor 24 of FIG. 3, sinusoidal cage 42 is able to expand from a delivery configuration suited for transluminal insertion into a patient's vasculature, to the deployed configuration of FIG. 4, wherein anchor 40 is adapted to engage an interior wall of the patient's vessel. The sinusoidal shape of anchor 40 is expected to facilitate rapid and reliable deployment and retrieval.

Figure 5A:
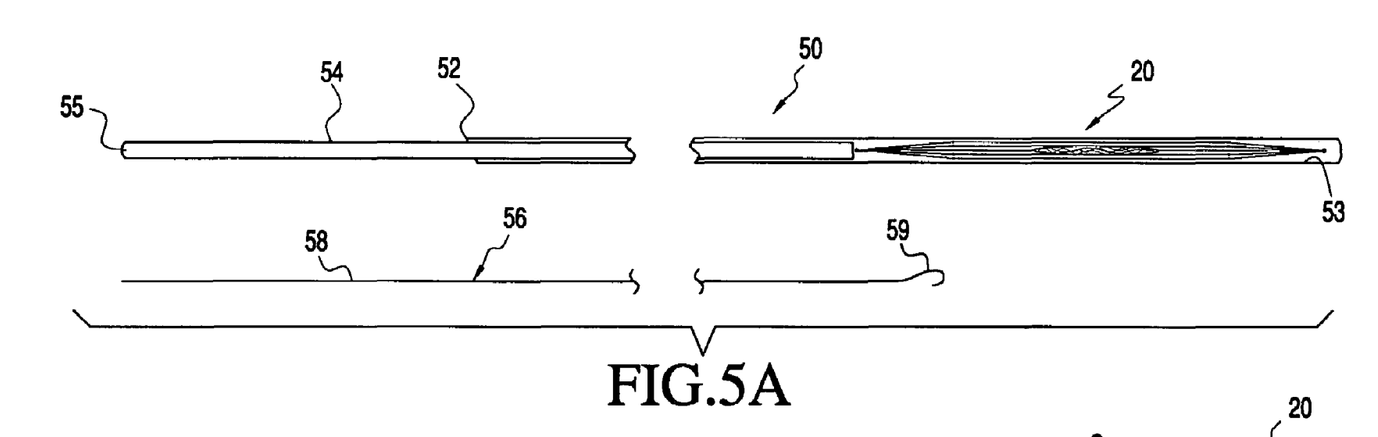
FIGS. 5A and 5B are views of delivery and retrieval apparatus of the present invention in use with the apparatus of FIG. 3, shown, respectively, in side-sectional view in a collapsed delivery configuration and in side view in an expanded deployed configuration.

Referring now to FIG. 5, delivery and retrieval apparatus of the present invention are described. Apparatus 50 comprises delivery sheath 52, pusher 54 and retriever 56, as well as apparatus 20 of FIGS. 3A and 3B. In FIG. 5A, pusher 54 and apparatus 20 are coaxially disposed within lumen 53 of sheath 52. Anchor 26 is not connected to pusher 54 and is adapted for semi-permanent implantation within a patient's vessel.

Figure 5B:
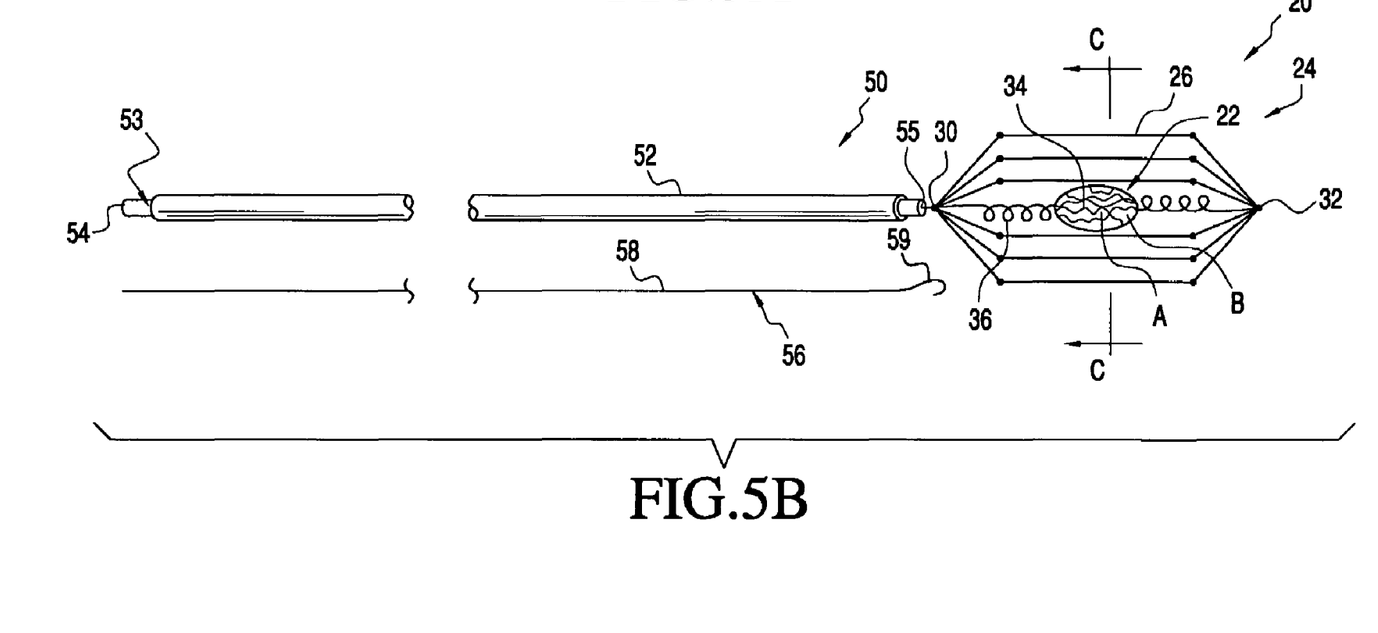

Anchor 24 is expanded by distally advancing pusher 54 to push the anchor out of lumen 53. Alternatively, sheath 52 may be proximally retracted while pusher 54, which abuts anchor 26, is held stationary, thereby pushing the anchor out of the sheath. Anchor 26 then resiliently expands to the deployed configuration of FIG. 5B. Anchor 24 and pellet 34 are implanted within the vessel for a predetermined period of time, after which the pellet may be removed from the patient's vasculature with retriever 56.

Retriever 56 comprises elongated member 58, which terminates at a distal end in hook 59. In order to retrieve apparatus 20, pusher 54 is removed from lumen 53 and replaced by retriever 56. Hook 59 may then be advanced beyond the distal end of sheath 52 and into the interior of anchor 24, then retracted such that it engages the anchor at joint 30. Continued retraction causes anchor 26 to collapse back to the delivery configuration of FIG. 5A within sheath 52. Retriever 56 may alternatively be advanced through optional lumen 55 of pusher 54.

Figure 6A:
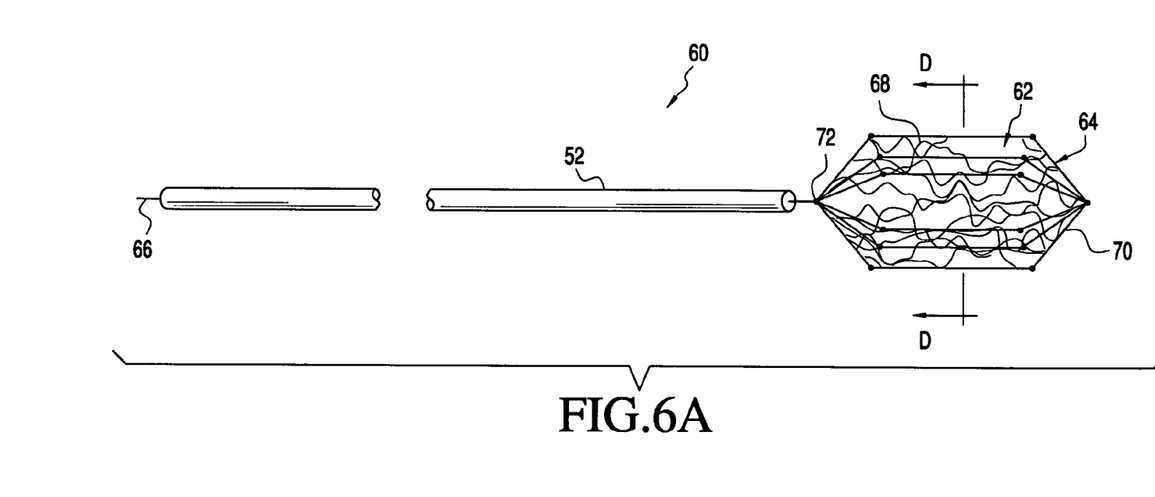
FIGS. 6A-6C are views of an alternative embodiment of the apparatus of FIG. 5 shown, respectively, in side view in an expanded deployed configuration, in cross-section along sectional view line C-C of FIG. 6A, and in side-sectional view in a collapsed delivery configuration.
Figure 6B:
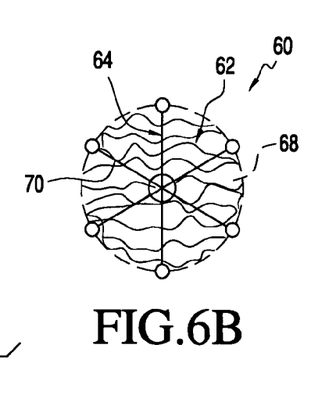
Figure 6C:
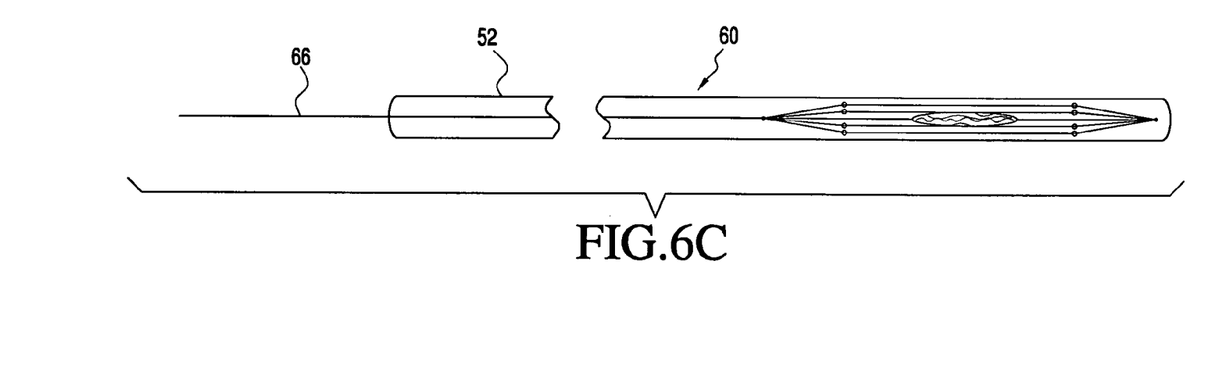

With reference to FIG. 6, an alternative embodiment of apparatus of the present invention, suited for temporary implantation, is described. Apparatus 60 comprises eluting or secreting material 62, anchor 64, delivery sheath 52, and guide wire 66. Material 62 comprises spongy material 68 disposed within anchor 64.

Anchor 64 comprises a collapsible cage, which is identical to the cage of anchor 24 described hereinabove, except that anchor 64 is attached to guide wire 66 at proximal joint 72 to provide rapid retrieval of apparatus 60 after temporary implantation. Spongy material 68 and anchor 64 collapse for delivery within sheath 52, as seen in FIG. 6C, and resiliently expand when delivered within the vasculature, as seen in FIGS. 6A and 6B. Spongy material 68 may, for example, be fabricated from an expandable and porous foam, swellable hydrogel matrix, minature mechanical infusion system designed utilizing nanotechnology/MEMS or biocompatible metal alloy filaments. Material 62 comprises a bioactive substance, as described hereinabove, and may optionally further comprise an anti-clotting, anti-thrombotic or anti-endothelialization agent, also described previously. As seen in FIG. 6C, material 62 covers a substantial portion of the patient's vessel in the expanded configuration, thereby exposing the bioactive substance to a substantial portion of blood passing therethrough.

Figure 7A:
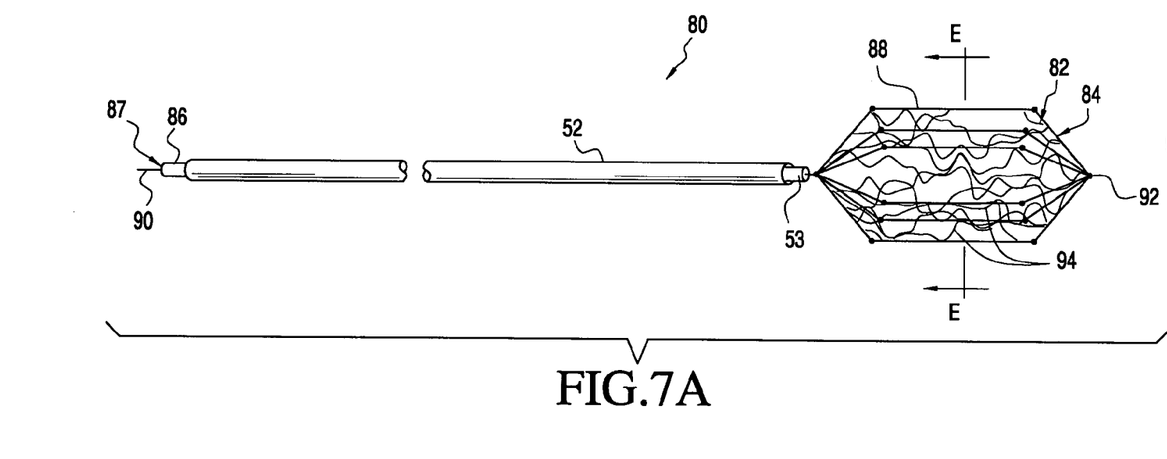
FIGS. 7A-7C are views of another alternative embodiment shown, respectively, in side view in an expanded deployed configuration, in cross-section along sectional view line D-D of FIG. 7A, and in side-sectional view in a collapsed delivery configuration.
Figure 7B:
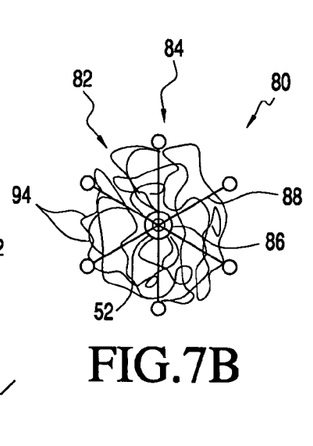
Figure 7C:
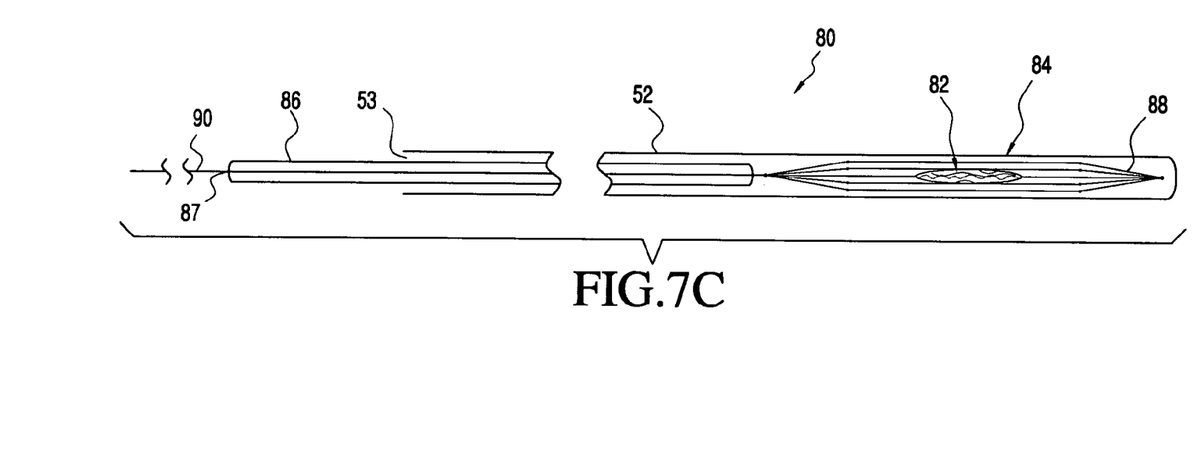

Referring now to FIGS. 7A-7C, another alternative embodiment of apparatus in accordance with the present invention is described. Apparatus 80 comprises eluting or secreting material 82, anchor 84, and guide tube 86, as well as delivery sheath 52. Guide tube 86 is coaxially disposed within lumen 53 of sheath 52. Anchor 84 comprises collapsible cage 88, which is attached to guide tube 86. Cage 88 is similar to the cages of the preceding embodiments, except that cage 88 connects to guide tube 86 in a manner that provides access to the interior of cage 88 through lumen 87 of tube 86.

Eluting or secreting material 82 comprises floppy elongated member 90, which passes through lumen 87 of tube 86 into the interior of cage 88, and is coupled at a distal end to joint 92 of cage 88. With cage 88 deployed in a patient's vessel, member 90 may be advanced while tube 86 is held stationary. Advancement causes member 90 to buckle, due to its attachment to joint 92 of cage 88. Continued advancement creates multiple turns 94 of material 82, which preferably occupy a substantial portion of the interior of cage 88, as seen in FIGS. 7A and 7B. Multiple turns 94 are coated with one or more bioactive substances, as described hereinabove.

Apparatus 80 may be retrieved by proximally retracting elongated member 90 to remove turns 94 from the interior of cage 88. Cage 88 may then be collapsed within lumen 53 of delivery sheath 52 to facilitate delivery and retrieval from a patient, as seen in FIG. 7C.

Figure 8A:
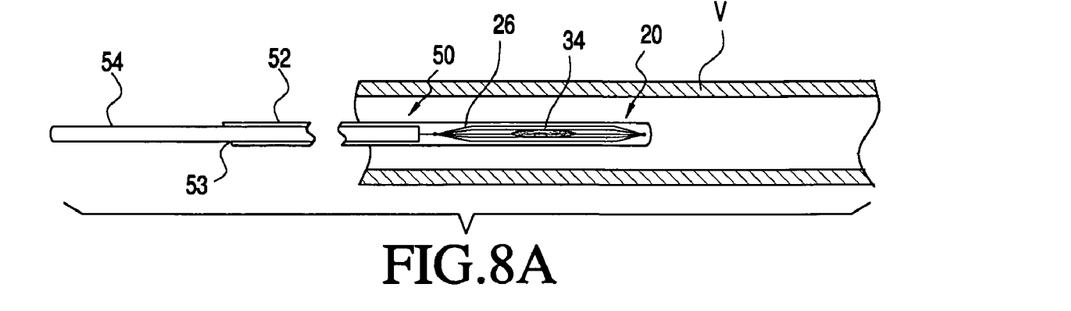
FIGS. 8A-8D are side-sectional views of the apparatus of FIG. 5 within a patient's vasculature demonstrating a method of use.

Referring now to FIGS. 8A-8D, a method of using the apparatus of FIG. 5 is described. As seen in FIG. 8A, with anchor 24 and pellet 34 in the delivery configuration within delivery sheath 52, apparatus 20 is advanced into a patient's vessel V using known percutaneous access techniques. Anchor 24 and pellet 34 then are expanded to the deployed configuration by distally advancing pusher 54 while delivery sheath 52 is held stationary, thereby advancing anchor 24 out of lumen 53 and beyond a distal end of delivery sheath 52. Alternatively, pusher 54 may be held stationary while delivery sheath 52 is proximally retracted releasing 24 out of lumen 53.

Figure 8B:
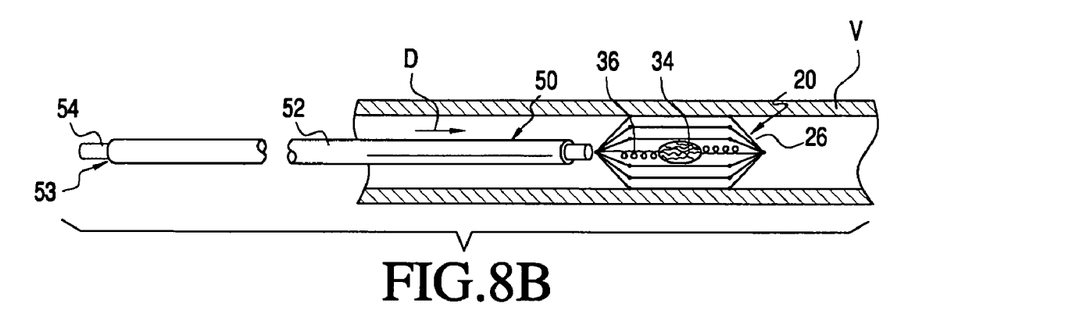

As seen in FIG. 8B, anchor 24 resiliently expands to the deployed configuration, while water swellable pellet 34 expands upon contact with blood flowing through vessel V. The resiliency of joints 30 and 32, as well as the resiliency of extensible band 36, preferentially orient anchor 24 in the deployed configuration, thereby establishing a lower energy state. Anchor 24 engages an interior wall of vessel V and anchors pellet 34 in position within a region of high velocity bloodflow.

Blood flows through vessel V in direction D. As discussed previously, pellet 34 comprises one or more bioactive substances that elute or secrete bioactive agents, including drugs, naturally-occurring or synthetic hormones or proteins, gene vectors, etc. Pellet 34 and anchor 24 may in addition be coated or impregnated with an anti-clotting agent, such as heparin, coumadin, GP IIb/IIIa inhibitors, direct thrombin inhibitors or aspirin, to prevent clotting around or within apparatus 20 or anti-endothelialization drug.

Blood flows through pellet 34 and comes into contact with the bioactive substance, thereby exposing the cells, as well as downstream capillary beds, to the substance and providing localized therapy. Where the bioactive substance comprises gene therapy vectors, as much as 30% of blood flowing past pellet 34 is expected to incorporate the vectors. Gene therapies suited for such localized delivery and expression include angiogenesis and revascularization. Delivery sheath 52 and pusher 54 may be removed from the patient, and apparatus 20 may be left in place within the patient for as much as 4 weeks or longer if the struts are coated with an anti-proliferative agent.

Figure 8C:
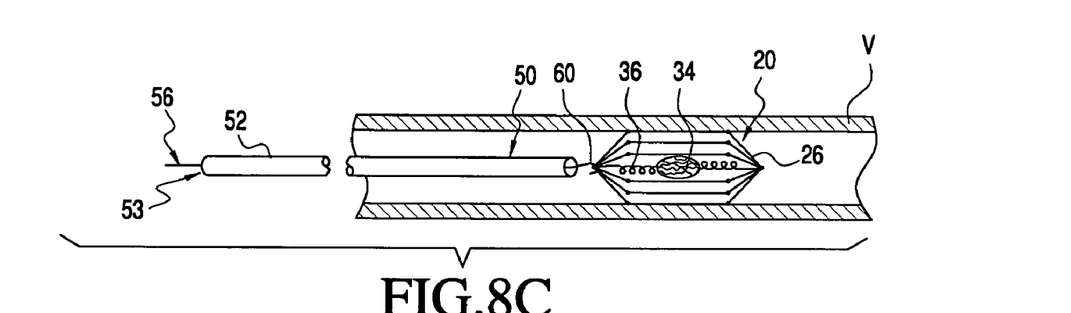

Upon completion of the procedure, sheath 52 is reintroduced into vessel V until it is disposed just proximal of anchor 24. Retriever 56 is advanced through lumen 53 beyond the distal end of sheath 52 and into the interior of anchor 24. Retriever 56 is then retracted proximally such that hook 60 engages joint 30 of anchor 24, as seen in FIG. 8C. Alternatively, a snare or other retrieval mechanism may be employed.

Figure 8D:
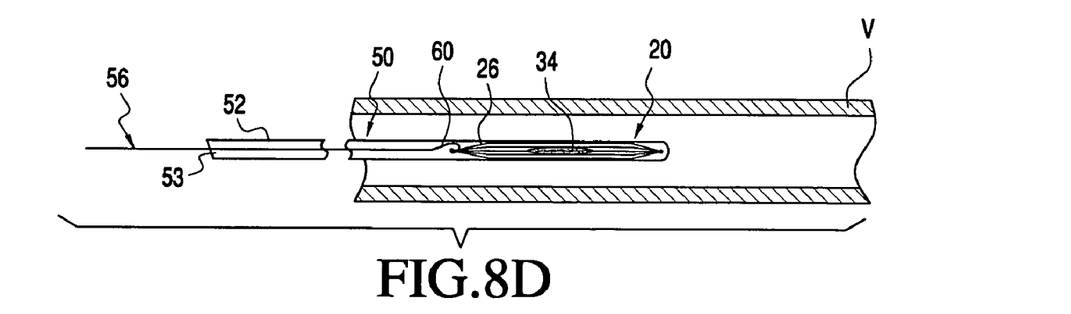

Continued retraction of retriever 56 collapses apparatus 20 back to the delivery configuration within sheath 52, as in FIG. 8D. Apparatus in accordance with the present invention may comprise one or more radiopaque features (not shown) to facilitate expansion or collapse of the anchor and eluting material. Apparatus 50 then is removed from vessel V.

Figure 9:
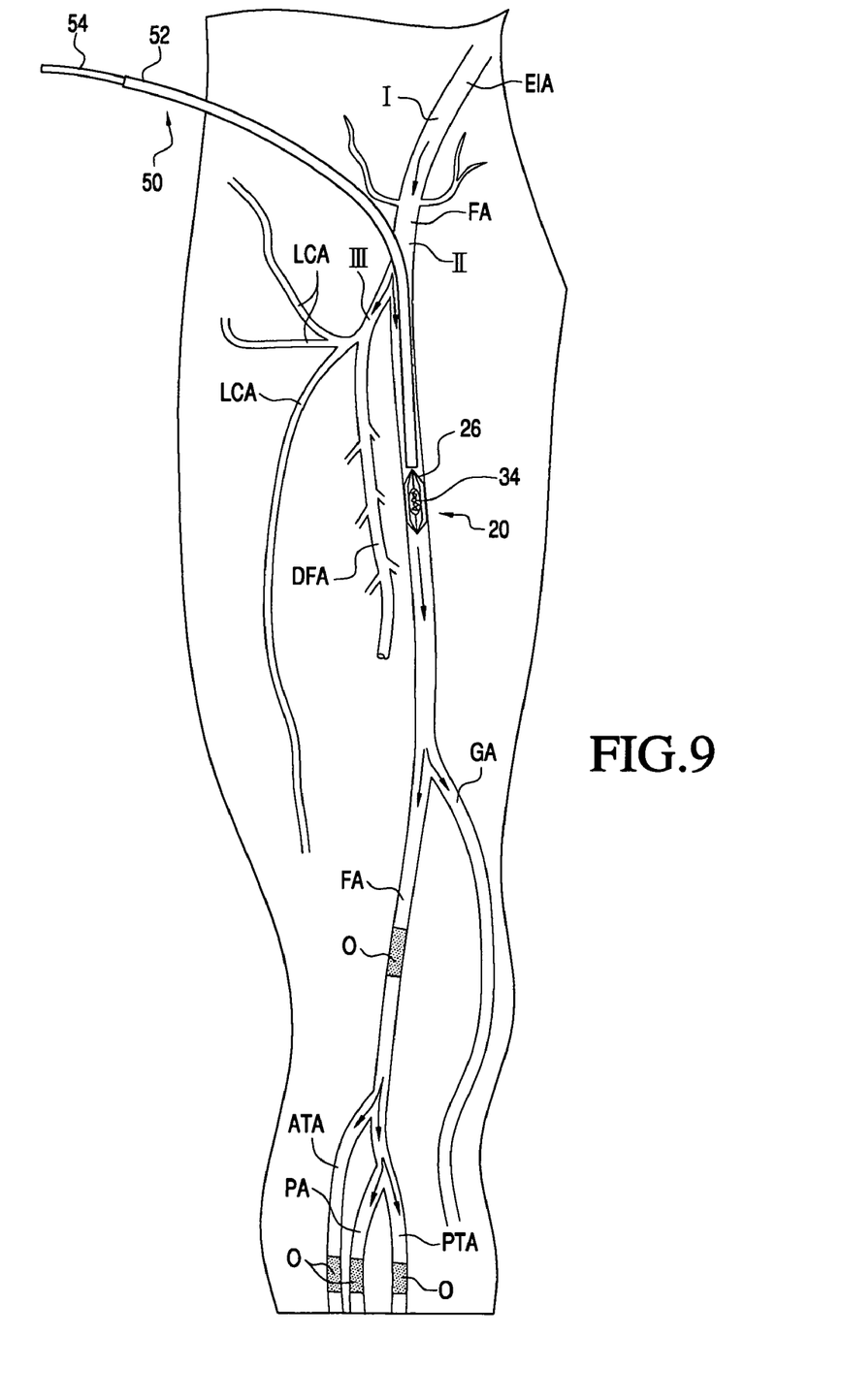
FIG. 9 is a side-sectional view of the apparatus of FIG. 5 within a patient's ischemic leg proximal of the patient's occluded superficial femoral artery, demonstrating a method of use in diffusing the occlusion.

With reference to FIG. 9, a method of using apparatus 50 in a drug delivery application to diffuse an occlusion in a patient's ischemic leg is described. FIG. 9 illustrates the primary arteries of the lower extremity, including the external iliac artery EIA, the superficial femoral artery FA, the lateral circumflex femoral artery LCA, the deep femoral artery DFA, the genicular artery GA, the anterior tibial artery ATA, the peroneal artery PA, and the posterior tibial artery PTA. The distal superficial femoral artery FA is shown occluded with occlusion O. The arteries distal of the femoral also may be occluded with occlusions O. If the occlusions are not diffused, the patient's leg below the occlusions will be unable to heal and may require amputation.

Catheter 50 is shown percutaneously introduced into the patient's vasculature just proximal to the bifurcation of the common femoral artery into the deep femoral and the superficial femoral arteries. With anchor 24 and pellet 34 disposed in the delivery state within sheath 52, apparatus 20 has been advanced distal of the split. Anchor 24 and pellet 34 are shown expanded to the deployed configuration via relative movement between pusher 54 and delivery sheath 52, so that anchor 24 engages the interior surface of superficial femoral artery FA.

Pellet 34 comprises a bioactive substance, as described hereinabove. In order to diffuse occlusions O, the bioactive substance may comprise a thrombolytic. Suitable thrombolytics include, for example, tissue plasminogen activator ("TPA"), streptokinase, and urokinase. Alternatively, the bioactive substance may comprise an anti-coagulant, for example, coumadin, heparin, aspirin, or GP IIb-IIIa inhibitors. In addition to diffusing occlusion O, anti-coagulants may be used to prevent clotting within and around cage 26 and pellet 34 during treatment. The bioactive substance may still further comprise an antiplatelet medication. Anti-coagulants, thrombolytics, and/or antiplatelet medications may also be used in conjunction with one another.

The bioactive substance eluted or secreted from pellet 34 is carried downstream by blood flowing in a direction illustrated by arrows in FIG. 9. The agent diffuses occlusion O to restore proper blood flow to the patient's lower leg by angiogenesis or other method. Apparatus 20 then may be collapsed back to the delivery state within sheath 52, and apparatus 50 may be removed from the patient, as described hereinabove.

Depending on the shape, size, severity, or location of occlusions O, or depending on any of a variety of other factors, anchor 24 alternatively may be deployed at or near locations marked I, II, and III in FIG. 9.

Figure 10:
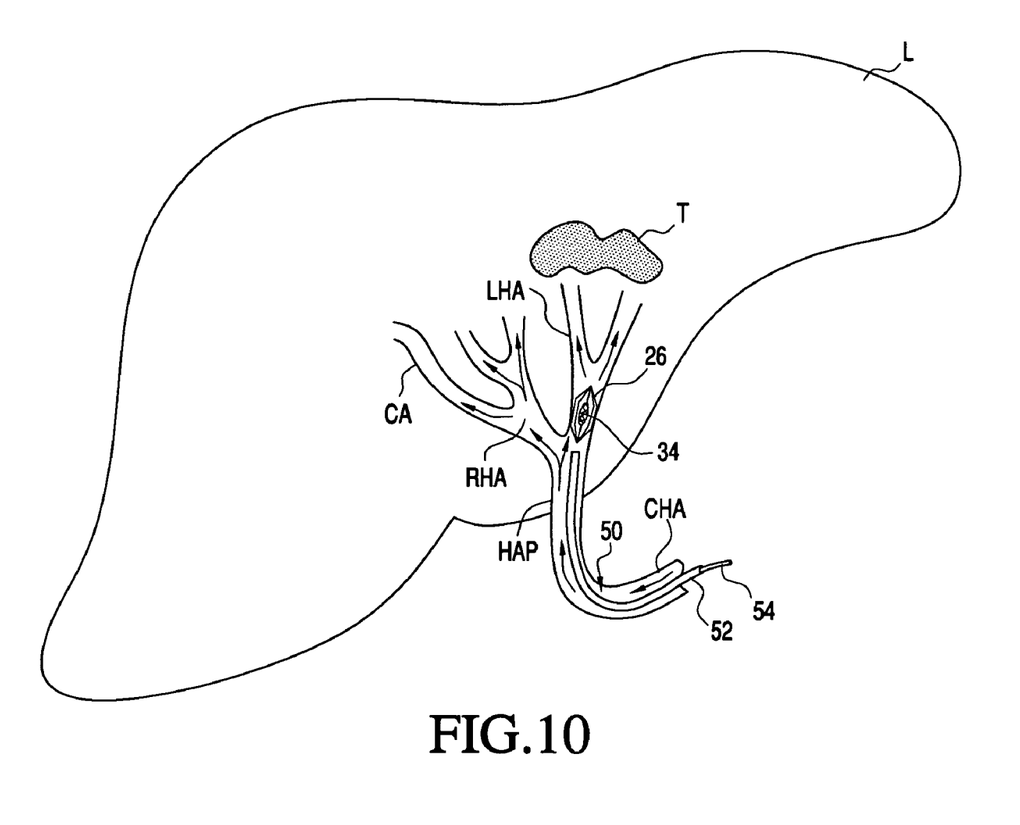
FIG. 10 is a side-sectional view of the apparatus of FIG. 5 within a patient's hepatic artery demonstrating a method of use in treating a tumor within the patient's liver.

Referring now to FIG. 10, a method of using apparatus 50 to treat tumorous tissue is described. FIG. 10 illustrates the primary arteries of a patient's liver L, including the common hepatic artery CHA, the hepatic artery proper HAP, the right hepatic artery RHA, the cystic artery CA (which feeds into the gallbladder), and the left hepatic artery LHA. Liver L includes tumorous tissue T just distal of left hepatic artery LHA, for which therapy is required.

Apparatus 50 has been percutaneously advanced and deployed within the left hepatic artery. Anchor 24 with pellet 34 comprising a suitable bioactive substance engages an interior wall of left hepatic artery LHA. Blood flowing through the artery, in a direction illustrated by arrows in FIG. 10, passes through pellet 34, thereby contacting the bioactive substance on its path to tumorous tissue T. According to other embodiments, apparatus 50 may be placed in the spleenic artery for systemic treatment. Similarly the device may be placed in any vessel that supplies arterial support to a tumor (i.e. Bronchial or pulmonary artery for lung cancer, cerebral artery for brain tumor, etc.). As described above, the bioactive substance may comprise a gene therapy or a drug therapy, or both. With gene therapy, the agent seeks to kill the cancerous tissue by halting expression at the genomic level, for example, halting replication of new cancer cells. With drug therapy, the agent seeks to kill the tumorous tissue by poisoning it.

Referring now to FIGS. 11A to 11E, a method of treating atherosclerotic disease using an alternative embodiment of apparatus 20 of the present invention is described. In the embodiment of FIG. 11, anchor 24' comprises a cage comprising longitudinally-extending struts 26' and radially-extending struts 28'. Rather than being welded to one another at their proximal and distal ends, respectively, radially-expanding struts 28' are joined by beads 30' of bioabsorbable material. As described hereinafter, when beads 30' dissolve, after a period of weeks to months, the radially-extending struts 28' reconfigure to lie against the wall of vessel V. In addition, pellet 34' and filament 36' are in this embodiment also bioabsorbable, so that these components dissolve over a period of weeks to months after implantation.

Figure 11A:
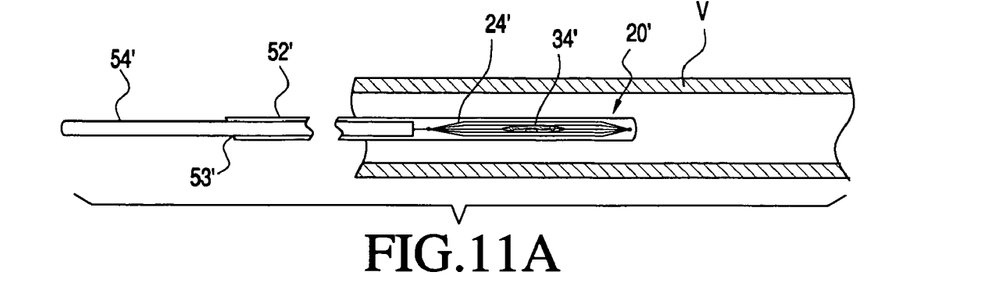
FIGS. 11A-11E are, respectively, side views of a reconfigurable embodiment of the present invention for use in a patient's inferior vena cava or other venous structure.

In FIG. 11A, anchor 24' and pellet 34' in the delivery configuration within delivery sheath 52', is shown being delivered into a patient's vessel V, such as the inferior vena cava, using known percutaneous access techniques. Anchor 24' and pellet 34' then are expanded to the deployed configuration by distally advancing pusher 54' while delivery sheath 52' is held stationary, thereby advancing anchor 24' out of lumen 53' and beyond a distal end of delivery sheath 52'. Alternatively, pusher 54' may be held stationary while delivery sheath 52' is proximally retracted releasing anchor 24' out of lumen 53'.

As depicted in FIG. 8B, anchor 24' resiliently expands to the deployed configuration, while pellet 34' contacts with blood flowing through vessel V. Struts 26' and 28' preferentially orient anchor 24' in the deployed configuration, so that anchor 24' engages an interior wall of vessel V and anchors pellet 34' in position within a region of high velocity bloodflow. Blood flows through vessel V in direction D.

Figure 11B:
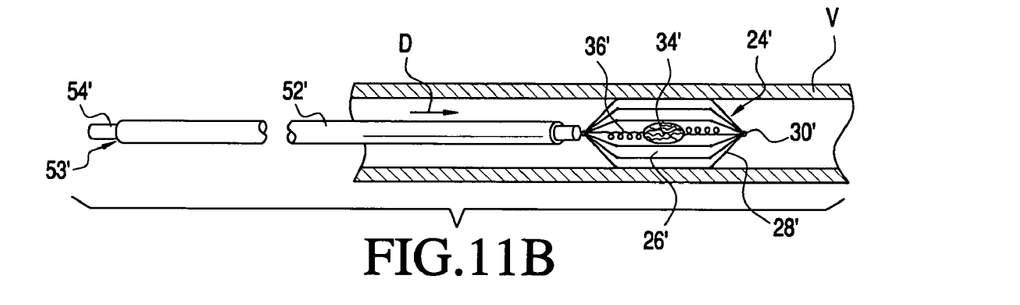

In an embodiment intended to inhibit or reverse atherosclerosis, pellet 34' preferably comprises a culture medium capable of maintaining and nourishing agents that propagate the apo-AI (Milano) or similar protein. Pellet 34' therefore comprises a material that is capable of extracting nutrients from blood flowing around the pellet, and secreting back into the blood the manufactured protein. Alternatively, pellet 34' may comprise a bioabsorbable material that is impregnated with the desired protein, so that the protein is released into the flood stream over a period of weeks to months as pellet 34' dissolves. The IVC may lack adequate oxygen partial pressure to support the cell culture, thus an arterial station may be preferable (i.e. arterial supply to the spleen).

Pellet 34' also may comprises one or more other bioactive substances that elute or secrete bioactive agents, including drugs, naturally-occurring or synthetic hormones or proteins, gene vectors, etc. Pellet 34' and anchor 24' may in addition be coated or impregnated with an anti-clotting agent, such as heparin, coumadin, or aspirin, to prevent clotting around or within radially-extending struts 28'.

Figure 11C:
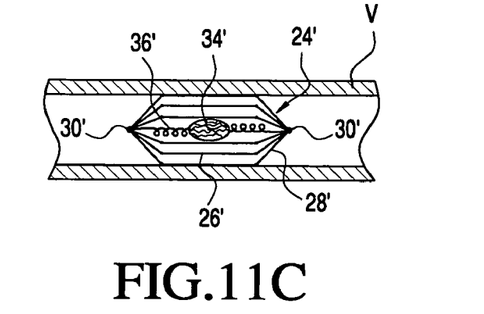

As shown in FIG. 11C, blood flows through pellet 34' and comes into contact with the bioactive substance, thereby exposing the downstream vasculature to the beneficial protein and/or drugs. Based on the limited data with apo-AI (Milano) proteins or equivalent reported in the literature, it is expected the continuous release of this protein from pellet 34' over the course of weeks to months may reduce atherosclerotic plaque build-up in the patient's vasculature, thereby restoring cardiovascular function and reducing the risk of stroke or localized ischemia, or cardiac infarct.

Figure 11D:
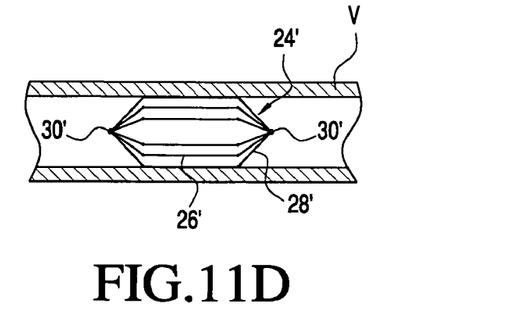
Figure 11E:
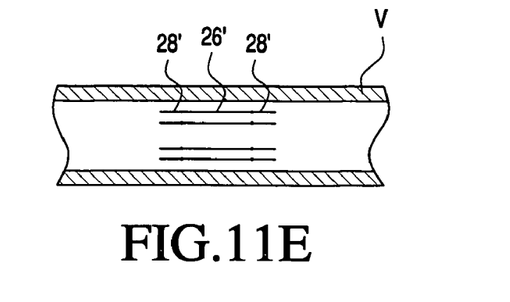

After a period of several weeks to months, pellet 34' and filament 36' dissolve completely, leaving the intact anchor depicted in FIG. 11D. During this process, longitudinally-extending struts 26' are expected to endothelialize to retain anchor 24' in position within the vessel. Finally, as depicted in FIG. 11E, after an additional period of time, for example, another several weeks, beads 30' dissolve. When this occurs, radially-extending struts 28' reconfigure so that they lie flat against the wall of vessel V, and subsequently the vessel endothelium envelops these struts as well. Consequently, unlike the anchor embodiment of FIG. 8, which was retrieved after a temporary period of implantation, anchor 24' of FIG. 11 is constructed to reconfigure after the pellet 34' dissolves, and requires no additional retrieval procedure.

According an additional aspect of the present invention, a lower profile anchor may be used to position the core matrix in the center of a vessel without the use of an expandable cage. For example, an anchor comprising two or more wire segments may be employed as a centering system to secure a micro-diagnostic chip or device. Similar to previous embodiments, nanotechnology can be used to position one or more small devices on the anchor. Suitable uses for the micro-diagnostic chips or devices include, but are not limited to: (1) measuring pressure; (2) measuring blood chemistry levels; (3) measuring other blood properties; and (4) transmitting the results to an antenna or device disposed outside the body.

Figure 12A:
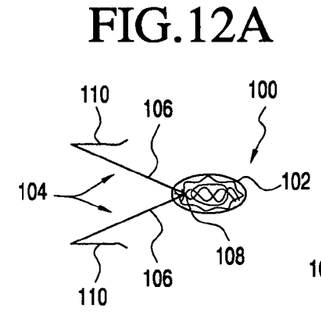
Figure 12B:
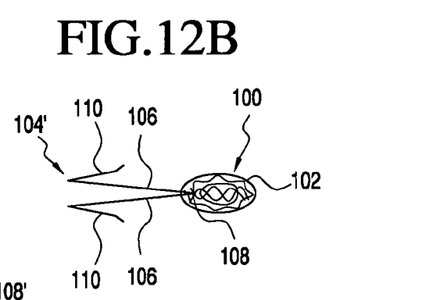

Referring to FIGS. 12A and 12B, apparatus 100 constructed in accordance with the principles of the present invention is described. Apparatus 100 preferably is configured to efficiently deliver a bioactive substance to the bloodstream within a vessel. Such a bioactive substance is absorbed by the blood more rapidly by positioning it at areas toward the center of the vessel lumen. Of course, blood flows with higher velocity toward the center of the vessel lumen. Apparatus 100 preferably is collapsible and expandable between an expanded profile depicted in FIG. 12A to a reduced delivery profile depicted in FIG. 12B.

In the illustrated embodiment, apparatus 100 comprises eluting or secreting material 102 attached to anchor 104. Anchor 104 comprises a pair of resilient legs 106 that meet at a hinge 108 disposed within material 102. To assist in retrieval of anchor 102, the legs may be coated or impregnated with a drug that prevents endothelialization. Radially extending barbs 100 extend radially from resilient legs 106 to prevent migration of the anchor once it is deployed in a vessel. Additional barbs or hooks may be added to further anchor the device and prevent migration, for example in the midst of antigrade flow. Anchor 104 may be fabricated from a nickel-titanium wire that is bent at hinge 108. In operation, anchor 104 is resiliently self-expanded from the reduced delivery profile (for transluminal insertion into a patient's vasculature) to the expanded profile (wherein anchor 104 engages an interior wall of the patient's vessel).

According to some embodiments, upon exposure to blood flow within a vessel, material 102 may expand to provide a high surface contact area for blood flowing at high velocity near the center of the vessel. Material 102 may comprise a bioactive substance that elutes or secretes a bioactive agent, such as a gene therapy sequences, drugs, proteins or hormones. For example, material may comprise an aggregation of autologous or donor cells, such as spleen cells, stem cells, isolated pancreatic islets or other cells, disposed in a matrix of a biocompatible culture medium capable of propagating or secreting naturally-occurring or synthetic proteins or hormones. After an anchor of the present invention is delivered within a patient's vasculature, blood contacts the material, which exposes the cells and downstream capillary beds to the substance, thereby providing localized or systemic therapy.

According to other embodiments material 102 may comprise a culture medium capable of nourishing and sustaining autologous or donor pancreatic cells or islets with nutrients extracted from the patient's bloodstream, and apparatus 100 may be implanted in an artery adjacent to the pancreas or hepatic vein. For treating atherosclerosis, material 102 may comprise a culture medium capable of propagating and secreting apolipoprotein A-I (Milano) or other HDL-like analog. Alternatively, material 102 may comprise a bioabsorbable material loaded with a drug, gene vector, synthetic hormone or protein or other bioactive agent that releases the bioactive agent into the bloodstream it dissolves. As a further alternative, the bioactive agent may be eluted from the material, and the apparatus later retrieved from the patient's vasculature.

Similar to previous embodiments, apparatus 102 may be impregnated or coated with an anti-clotting agent, such as heparin, coumadin, direct thrombin inhibitor, glycoprotein IIb IIIa inhibitor or aspirin, to prevent clotting or thrombus build-up. Alternatively, apparatus 102 may be coated or impregnated with an agent that promotes targeted cell death or clotting-off of the vessel to kill unwanted or diseased downstream tissue.

When used in drug delivery applications, the bioactive agent delivered from material 102 may comprise a therapeutic toxin such as a chemotherapy drug. Advantageously, the delivery of toxic drugs directly into the vasculature via sustained release (e.g., in an arterial division supplying a tumor) provide more focused therapy than conventional methods. According to other embodiments, the bioactive agent may comprise antibiotics, wherein antibiotics are beneficially delivered directly into an abscess or infected area. According to further embodiments, apparatus 102 is disposed in a central vein of the patient's vasculature to provide prolonged systemic delivery of a desired bioactive agent. Apparatus 102 may also be deployed in a central vein and then removed at a later time, thereby providing systemic treatment to the patient to eliminate the risk of infection from prolonged IV use.

Figure 13:
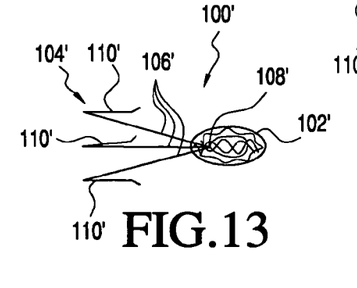
FIG. 13 is a side view of an alternative apparatus for delivering a bioactive substance within a patient's bloodstream.

Referring to FIG. 13, apparatus 100' comprises eluting or secreting material 102' attached to anchor 104'. Anchor 104' comprises three resilient legs 106' having barbs 110' disposed at distal ends thereof. According to some embodiments, apparatus 100' comprises additional resilient legs to provide additional anchor stability and engagement with the vessel wall. As would be understood by those of skill in the art, apparatus 100' may include any number of additional resilient legs without departing from the scope of the present invention.

Figure 14A:
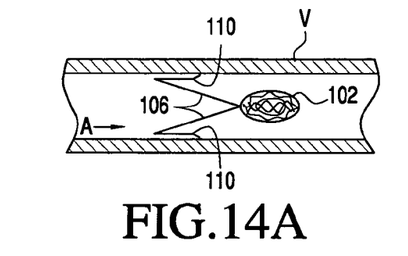
FIGS. 14A-14F are side-sectional views depicting a method of retrieving the apparatus of FIG. 12 from a patient's vessel.

Referring to FIG. 14A, apparatus 100 is depicted within a patient's blood vessel V, wherein blood flow direction is indicated by arrow A. The central location of material 102 within vessel V advantageously exposes the bioactive substance to bloodflow of relatively high velocity. Barbs 110 extend from resilient legs 106 into the vessel wall, thereby fixing the apparatus within vessel V at a selected location.

Figure 14B:
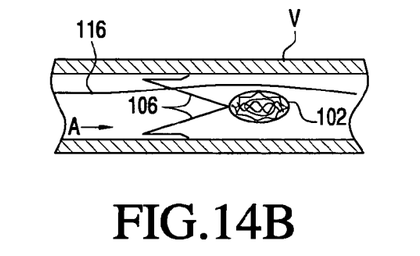
Figure 14C:
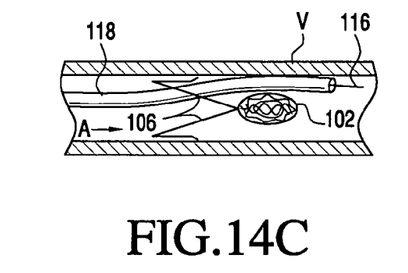

Referring to FIGS. 14B-14F, a method of retrieving apparatus 100 from a vessel will now be described. Referring to FIG. 14B, a guide wire 116 is initially advanced transluminally into vessel V such that a distal tip of guide wire 116 is positioned distal of apparatus 100. Referring to FIG. 14C, catheter 118 having a lumen is advanced over the guide wire such that a distal tip of catheter 118 is positioned distal of apparatus 100.

Figure 14D:
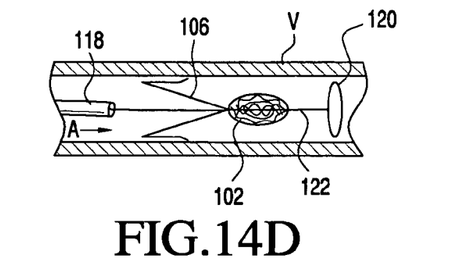

Referring to FIG. 14D, guide wire 116 is retracted and a retrieval element is deployed from the distal end of the catheter. Catheter 118 may be retracted or partially retracted at this time. In the illustrated embodiment, the retrieval element comprises a resilient loop 120 attached at the distal end of a length of wire 122. According to some embodiments, resilient loop 120 automatically expands from a reduced delivery profile to an expanded profile as it exits the confines of the catheter lumen.

Figure 14E:
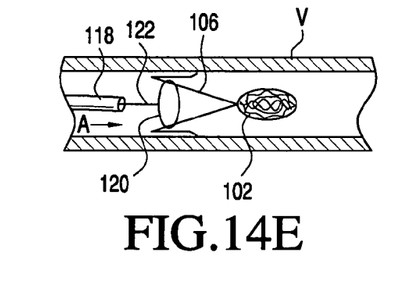
Figure 14F:
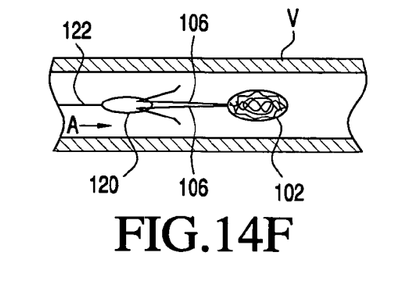

Referring to FIG. 14E, resilient loop 120 is retracted proximally, thereby snaring apparatus 100. More particularly, resilient loop 120 is retracted over material 102 and legs 106 until the loop catches on barbs 110. Referring to FIG. 14F, further retraction of resilient loop 120 preferably causes the resilient legs to collapse radially inward toward the center of vessel V, thereby unhooking the barbs from the vessel wall. The collapsed apparatus is then retracted, for example through the catheter lumen. As would be appreciated by those of skill in the art, many other retrieval elements may be employed without departing from the scope of the present invention.

Figure 15:
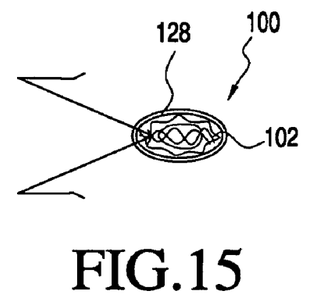
FIG. 15 is a side view of a further alternative apparatus for delivering a bioactive substance within a patient's bloodstream.
Figure 16:
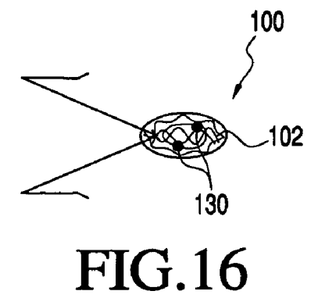
FIG. 16 is a side view of yet another alternative apparatus for delivering a bioactive substance within a patient's bloodstream.

Referring to FIG. 15, according to some embodiments of the present invention, an outside layer 128 is formed around material 102. Outside layer 128 may comprise a porous material that is coated with a drug that prevents biologic material from adhering to its surface. Referring to FIG. 16, according to other embodiments, nanotechnology is employed to implant one or more small devices or sensors 130 into material 102. Sensors 130 may be used to measure temperature, pressure and other physiological and/or biochemical properties in the blood stream, and then transmit the acquired information to a receiving device outside the patient's body.

Figure 17A:
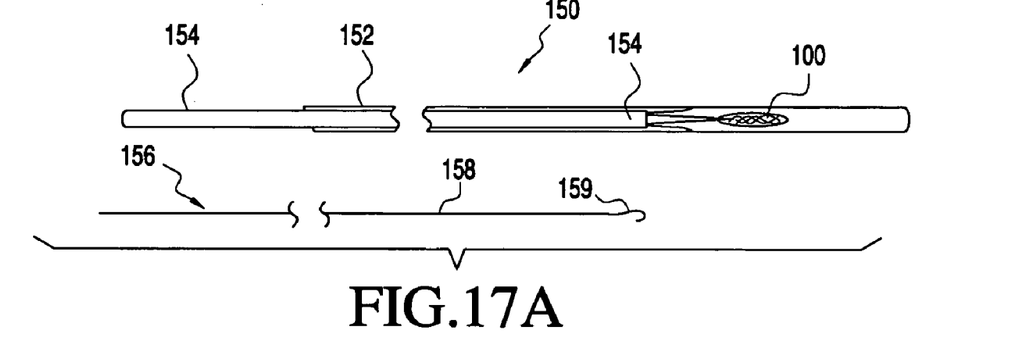
FIGS. 17A and 17B are views of delivery and retrieval apparatus of the present invention in use with the apparatus of FIG. 12, shown, respectively, in side-sectional view in a collapsed delivery configuration and in side view in an expanded deployed configuration.

Referring to FIGS. 17A and 17B, an exemplary delivery system 150 for delivering apparatus 100 will now be described. In FIG. 17A, pusher 154 and apparatus 102 are coaxially disposed within lumen 153 of sheath 152. Apparatus 100, which is not connected to pusher 154, is adapted for semi-permanent implantation within a patient's vessel. Apparatus 100 is expanded by distally advancing pusher 154 to push the anchor out of lumen 53. Alternatively, sheath 152 may be proximally retracted while pusher 154 is held stationary, thereby pushing the anchor out of the sheath.

Figure 17B:
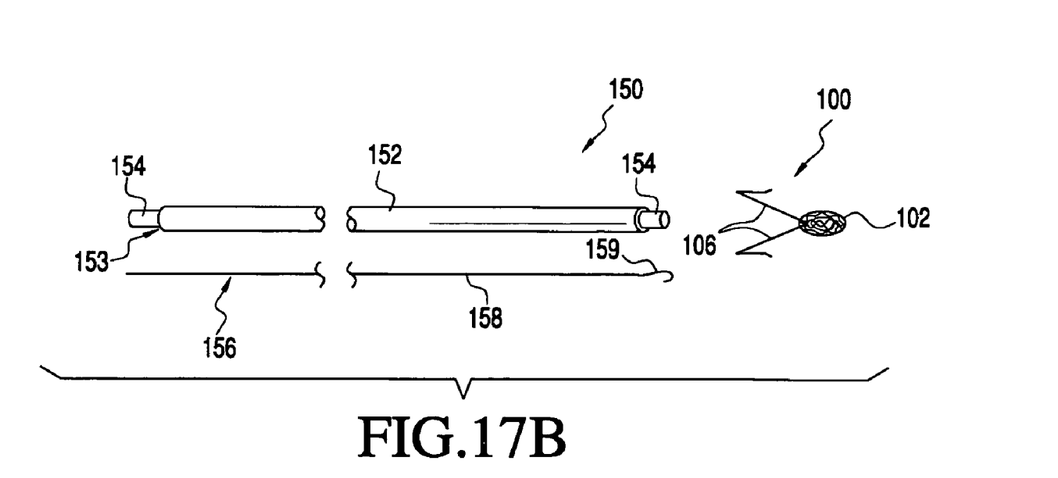

Referring to FIG. 17B, as apparatus 100 is pushed out of sheath, it resiliently expands to the deployed configuration. Apparatus 102 and material 102 are implanted within the vessel for a predetermined period of time, after which the apparatus may be removed from the patient's vasculature with retriever 156. Retriever 156 comprises elongated member 158, which terminates at a distal end in hook 159. In order to retrieve apparatus 100, pusher 154 is removed from lumen 153 and replaced by retriever 156. Hook 159 may then be advanced beyond the distal end of sheath 152 and used to capture or snare the apparatus, for example by hooking one of the barbs on the resilient legs. Retraction causes apparatus 100 to collapse back to the reduced delivery profile. Alternatively, a resilient loop such as described with respect to FIG. 14 may be employed as the retriever.

Although particular embodiments of the present invention have been described above in detail, it will be understood that this description is merely for purposes of illustration. Specific features of the invention are shown in some drawings and not in others; this is for convenience only, and any feature may be combined with another in accordance with the invention. Further variations will be apparent to one skilled in the art in light of this disclosure. Likewise, a variety of alternative eluting materials and bioactive substances will be apparent to those of skill in the art. These and other variations are intended to fall within the scope of the appended claims.

What is claimed is:

1. Apparatus for treating atherosclerotic disease, the apparatus comprising:
   a delivery sheath having proximal and distal ends, and a lumen extending therebetween;
   an anchor expandable from a delivery configuration adapted for disposition within the delivery sheath lumen, to a deployed configuration adapted for engagement of an interior surface of a vessel;
   an advancement device disposed within the delivery sheath lumen and extending proximal of the proximal end of the delivery sheath, the advancement device configured to expand the anchor from the delivery configuration to the deployed configuration; and
   a matrix disposed within the anchor, the matrix comprising a material adapted to elute or secrete a bioactive agent.

2. The apparatus of claim 1 wherein the anchor is adapted for disposition within the lumen in the delivery configuration.

3. The apparatus of claim 1 further comprising a retriever disposed within the delivery sheath lumen and extending proximal of the proximal end of the delivery sheath, the retriever configured to collapse the anchor from the deployed configuration to the delivery configuration.

4. The apparatus of claim 1 wherein the matrix comprises a culture medium for propagating the bioactive agent.

5. The apparatus of claim 1 wherein the matrix comprises a bioabsorbable material that elutes or secretes the bioactive agent during dissolution of the bioabsorbable material.

6. The apparatus of claim 1, wherein the anchor is coated or impregnated with a drug chosen from the group consisting of thrombolytics, anticoagulants, antiplatelet medications and antibiotics.

7. The apparatus of claim 1, wherein the advancement device is coupled to a proximal end of the anchor.

8. The apparatus of claim 7, wherein the anchor is collapsible back to the delivery configuration.

9. The apparatus of claim 1, wherein the anchor comprises a resiliently expandable cage.

10. The apparatus of claim 1, wherein the anchor comprises a pair of resilient expandable legs.

11. The apparatus of claim 10, wherein each resilient leg includes one or more barbs to provide improved engagement with the vessel.

12. The apparatus of claim 1, wherein the anchor comprises three or more resilient expandable legs that are connected at a hinge.

13. The apparatus of claim 12, wherein each resilient leg includes one or more barbs to provide improved engagement with the vessel.

14. The apparatus of claim 1 wherein the anchor includes a plurality of struts joined at proximal and distal ends by bioabsorbable beads, the bioabsorbable beads comprising a material that dissolves after a predetermined time to permit the plurality of struts to reconfigure.

15. The apparatus of claim 1, wherein one or more sensors are embedded within the material.

16. The apparatus of claim 15, wherein the sensors are used to measure physiological and biochemical properties in the blood stream, and then transmit the information concerning the physiological and biochemical properties to a receiving device.

17. The Apparatus of claim 1, wherein the anchor is adapted to engage the matrix while in the delivery configuration.

18. Apparatus for treating atherosclerotic disease, the apparatus comprising:
   an anchor expandable from a delivery configuration adapted for disposition within a delivery sheath, to a deployed configuration adapted for engagement of an interior surface of a vessel, the anchor comprising a pair of resilient expandable legs, wherein each resilient leg includes one or more barbs to provide improved engagement with the vessel; and
   a matrix disposed within the anchor, the matrix comprising a material adapted to elute or secrete a bioactive agent.

19. Apparatus for treating atherosclerotic disease, the apparatus comprising:
   an anchor expandable from a delivery configuration adapted for disposition within a delivery sheath, to a deployed configuration adapted for engagement of an interior surface of a vessel, the anchor comprising a plurality of struts joined at proximal and distal ends by bioabsorbable beads; and
   a matrix disposed within the anchor, the matrix comprising a material adapted to elute or secrete a bioactive agent,
   wherein the bioabsorbable beads comprise a material that dissolves after a predetermined time to permit the plurality of struts to reconfigure.

20. Apparatus for treating atherosclerotic disease, the apparatus comprising:
   an anchor expandable from a delivery configuration adapted for disposition within a delivery sheath, to a deployed configuration adapted for engagement of an interior surface of a vessel; and
   a matrix disposed within the anchor, the matrix comprising a material adapted to elute or secrete a bioactive agent,
   wherein one or more sensors are embedded within the material.

* * * * *